US011253150B2

(12) United States Patent
Ranchod et al.

(10) Patent No.: US 11,253,150 B2
(45) Date of Patent: Feb. 22, 2022

(54) VISUALIZATION DEVICE WITH HANDED SYMMETRY

(71) Applicant: BROADSPOT IMAGING CORP, Richmond, CA (US)

(72) Inventors: Tushar M. Ranchod, Berkeley, CA (US); Scott Janis, El Cerrito, CA (US); Andre E. Adams, Tiburon, CA (US); Germain Verbrackel, San Francisco, CA (US); Benjamin A. Jacobson, Santa Barbara, CA (US); Clint Suson, San Francisco, CA (US)

( * ) Notice: Subject to any disclaimer, the term of this patent is extended or adjusted under 35 U.S.C. 154(b) by 111 days.

(21) Appl. No.: 16/433,987

(22) Filed: Jun. 6, 2019

(65) Prior Publication Data

US 2020/0069182 A1     Mar. 5, 2020

Related U.S. Application Data

(60) Provisional application No. 62/685,053, filed on Jun. 14, 2018.

(51) Int. Cl.
*A61B 3/14* (2006.01)
*A61B 3/00* (2006.01)
*H04N 5/262* (2006.01)

(52) U.S. Cl.
CPC ............ *A61B 3/14* (2013.01); *A61B 3/005* (2013.01); *H04N 5/2628* (2013.01)

(58) Field of Classification Search
CPC ......... H04N 3/14; H04N 3/005; H04N 5/2628
See application file for complete search history.

(56) References Cited

U.S. PATENT DOCUMENTS

| | | | |
|---|---|---|---|
| 7,862,173 B1 | 1/2011 | Ellman | |
| 2010/0252294 A1* | 10/2010 | Kondo | H01M 50/20 173/217 |
| 2010/0278394 A1 | 11/2010 | Raguin et al. | |
| 2015/0351623 A1* | 12/2015 | Watanabe | A61B 3/0041 351/206 |
| 2015/0366447 A1* | 12/2015 | Su | A61B 3/0008 351/206 |
| 2016/0242734 A1* | 8/2016 | Su | A61B 8/4427 |
| 2017/0239012 A1* | 8/2017 | Wood | A61B 1/0019 |
| 2018/0125449 A1* | 5/2018 | Mauldin, Jr | A61B 8/462 |

OTHER PUBLICATIONS

International Search Report & Written Opinion of the International Searching Authority dated Aug. 27, 2019 as received in Application No. PCT/US2019/36189.

\* cited by examiner

*Primary Examiner* — Mohammed A Hasan

(57) ABSTRACT

A device may include a display screen and a generally triangular shaped body with first, second, and third sides, where the display screen may be generally parallel with the first side. The device may be configured such that either of the second side and third side may be oriented generally upwards during operation. The device may also include a sensor configured to detect whether the second or the third side is oriented generally upwards, and a computing device configured to orient an image to be displayed on the display screen based on whether the second or the third side is oriented generally upwards.

19 Claims, 8 Drawing Sheets

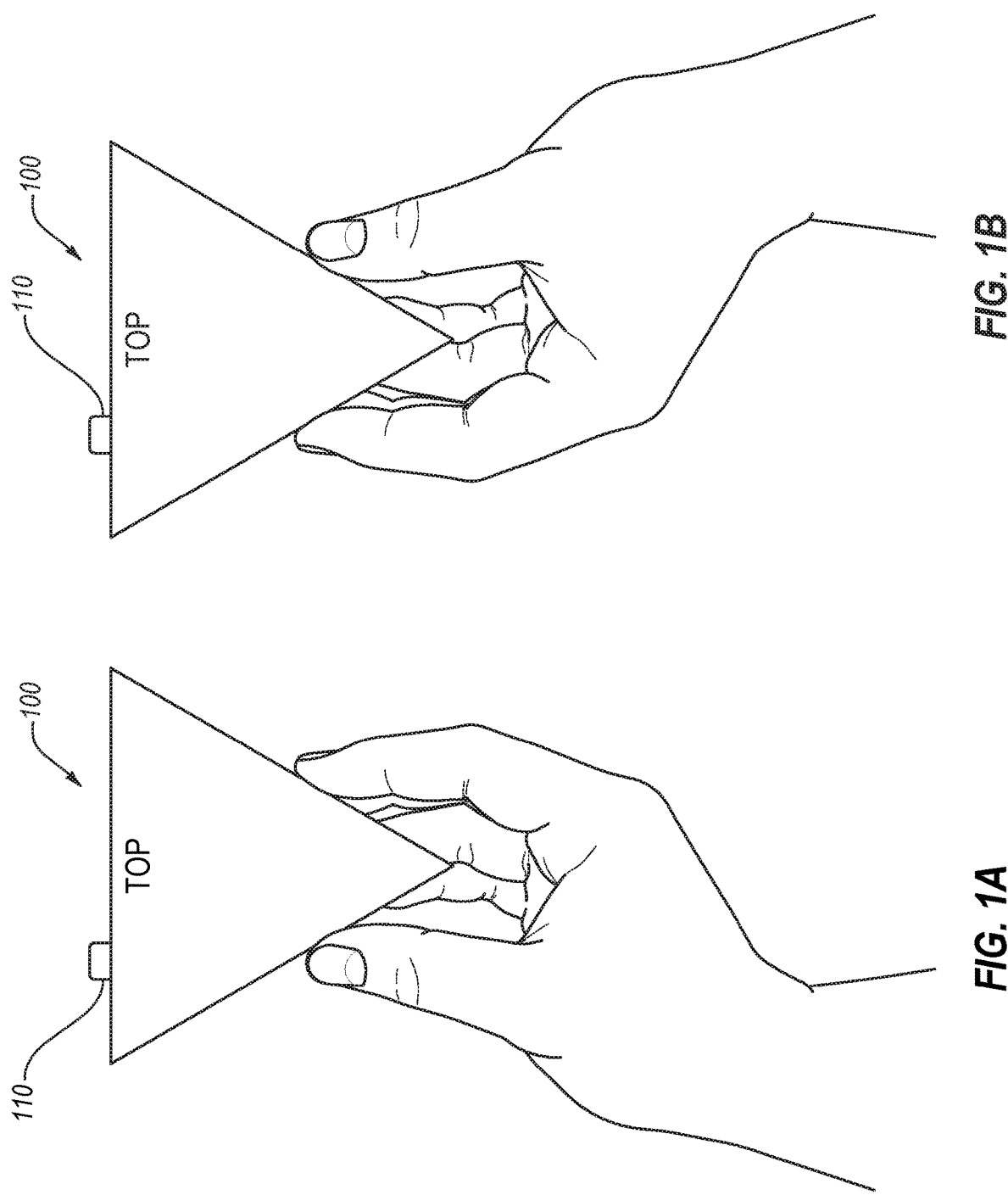

VISUALIZATION DEVICE WITH HANDED SYMMETRY

FIELD

The application relates generally to a visualization device with handed symmetry.

BACKGROUND

Ocular imaging is commonly used both to screen for diseases and to document findings discovered during clinical examination of the eye. Various devices may be used in ocular imaging. However, many of these devices are bulky machines that are difficult to operate.

The subject matter claimed herein is not limited to embodiments that solve any disadvantages or that operate only in environments such as those described above. Rather, this background is only provided to illustrate one example technology area where some embodiments described herein may be practiced.

SUMMARY

Embodiments of the disclosure include a device that includes a display screen and a generally triangular shaped body with first, second, and third sides, where the display screen may be generally parallel with the first side. The device may be configured such that either of the second side and third side may be oriented generally upwards during operation. The device may also include a sensor configured to detect whether the second or the third side is oriented generally upwards, and a computing device configured to orient an image to be displayed on the display screen based on whether the second or the third side is oriented generally upwards.

One or more of the devices of the present disclosure may also include a panel region proximate the display screen and projecting away from the generally triangular shaped body.

One or more of the devices of the present disclosure may be configured such that the panel region is generally contiguous with the first side of the generally triangular shaped body.

One or more of the devices of the present disclosure may also include a thumb pad spanning between the generally triangular shaped body and the panel region, the thumb pad shaped to interface with a thumb of either a left hand or a right hand.

One or more of the devices of the present disclosure may be configured such that the thumb pad is recessed into a casing of the device.

One or more of the devices of the present disclosure may also include a sensing device at an apex of the generally triangular shaped body, where the sensing device may be configured to sense a property of an eye.

One or more of the devices of the present disclosure may also include a disposable casing covering the sensing device.

One or more of the devices of the present disclosure may be configured such that the sensing device includes multiple imaging devices that image an eye through the apex of the generally triangular shaped body.

One or more of the devices of the present disclosure may be configured such that the display screen is removable.

One or more of the devices of the present disclosure may be configured such that the display screen is configured to tilt between zero and thirty degrees, where the tilt moves an edge of the display screen away from or in towards a plane of the first side.

One or more of the devices of the present disclosure may be configured such that the generally triangular shaped body includes a rounded triangular pyramid shaped body.

One or more of the devices of the present disclosure may be configured such that the generally triangular shaped body spans between one fourth and one half of an overall length of the device.

One or more of the devices of the present disclosure may also include a fin or finger grip region along a back side of the device, the back side of the device opposite from the display screen.

One or more of the devices of the present disclosure may also include one or more buttons on the back side of the device proximate the fin or finger grip region for controlling operation of the device.

One or more of the devices of the present disclosure may be configured such that the computing device is configured to orient the image such that a top of the image is oriented towards the second side when the second side is generally oriented upwards and the top of the image is oriented towards the third side when the third side is generally oriented upwards.

One or more embodiments of the present disclosure may include a device that includes a rounded triangular pyramid shaped body with first, second, and third sides, where the device may be configured such that either of the second side and the third side may be oriented generally upwards during operation. The device may also include a panel region projecting away from the rounded triangular pyramid and perpendicular with a plane of a base of the rounded triangular pyramid, where the panel region may include a slot with an opening at a distal end and a first data exchange port at a proximate end, where the proximate end is proximate the rounded triangular pyramid. The device may additionally include a removable display screen shaped to slide through the opening and into the slot of the panel region. The removable display screen may include a second data exchange port on a first end and a third data exchange port on a second end opposite the first end such that the second and third data exchange ports are configured to interface with the first data exchange port such that display data of the device is displayed on the removable display screen.

One or more of the devices of the present disclosure may be configured such that the removable display screen is generally symmetrical about a line from the first end to the second end aside from a location of the second and third data exchange ports.

One or more of the devices of the present disclosure may also include a sensing device, where the sensing device may include multiple imaging devices configured to image an eye through an apex of the generally triangular shaped body.

One or more of the devices of the present disclosure may be configured such that the removable display screen is configured to display an image of the display data in a first orientation if the first data exchange port is interfaced with the second data exchange port and in a second orientation if the first data exchange port is interface with the third data exchange port, the second orientation inverted relative to the first orientation.

One or more embodiments of the present disclosure may include a device that includes a multi-sided body with at least first, second, and third sides, where the device may be configured such that either of the second side and the third side may be oriented generally upwards during operation.

The device may also include a panel region extending away from the multi-sided body and perpendicular with a plane of a base of the rounded triangular pyramid. The device may additionally include a display screen disposed on an inside face of the panel region and perpendicular with a plane of a base of the multi-sided body. The device may also include a sensor configured to detect whether the second or the third side is oriented generally upwards, and a computing device configured to orient an image to be displayed on the display screen based on whether the second or the third side is oriented generally upwards.

BRIEF DESCRIPTION OF FIGURES

Example embodiments will be described and explained with additional specificity and detail through the use of the accompanying drawings in which:

FIGS. 1A and 1B illustrate an example of a device being held in left and right hands;

DESCRIPTION OF EMBODIMENTS

Figure 2B:
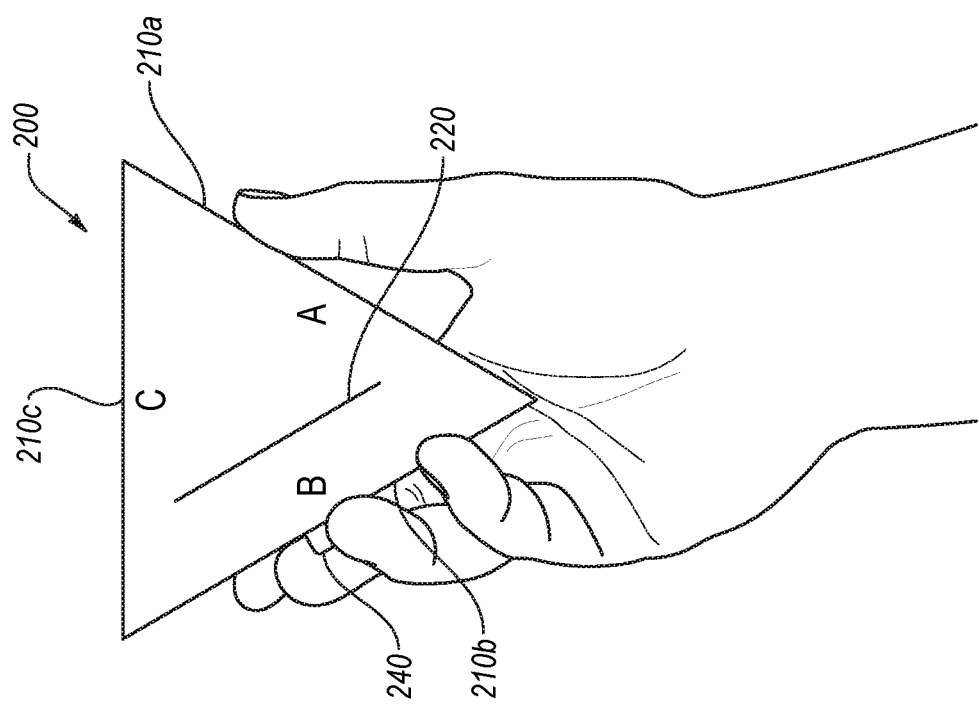
FIGS. 2A and 2B illustrate an example of another device being held in left and right hands.

Hand-held devices may be designed differently if the primary position of the user is in line with the device (e.g., the device is pointed directly towards or away from the user) as opposed to next to the device (e.g., the device is pointed sideways or obliquely relative to the user's face or body). If a device is generally oriented sideways or obliquely relative to the user, the user may desire to interact with a screen on the device such that the screen is facing the user while the device is oriented sideways or obliquely. Combining a useful and comfortable screen orientation in this scenario with symmetry that allows either right- or left-handed use is challenging.

The present disclosure relates to, inter alia, the use of a visualization device that is shaped and designed to operate in an effective manner regardless of whether the device is operated by the right hand or the left hand of a user. In particular, the visualization device may have a generally triangular shaped body such that the device may be gripped by a user. In addition, the visualization device may include a screen that is to be oriented towards the user during operation. Because of the triangular shape of the visualization device, as the device is shifted from one hand to the other, the screen may be oriented towards the user in either hand. However, such a shift may invert the screen such that the screen is upside down when operated in a right hand as compared to when operated in a left hand. The visualization device may include a sensor to detect the orientation of the device and orient any images on the screen (e.g., by inverting the image) to maintain a correct orientation depending on which hand is used by the user to hold and/or operate the device. Additionally or alternatively, the user may be able to press a button, invoke a control, or otherwise interact with the device to manually flip the image orientation on the screen.

FIGS. 1A and 1B illustrate an example of a device 100 being held in right and left hands, respectively. FIGS. 1A and 1B illustrate the device 100 with a top that is oriented upwards and with an artifact 110 on the top of the device 100.

As illustrated in FIG. 1A, when a user holds the device 100 with a top of the device being oriented upwards in a right hand, the artifact 110 of the device may be oriented towards the left side of the device (e.g., proximate the thumb of the right hand of the user). In contrast, as illustrated in FIG. 1B, when a user holds the device 100 with the top of the device oriented upwards in a left hand, the artifact 110 of the device may be oriented towards the left side of the device (e.g., proximate the fingers of the left hand of the user).

Depending on the artifact 110, this change in location depending on which hand is using the device 100 may be problematic. For example, if the artifact 110 is a display screen, it may be seen when used in one hand but not seen when used in the other hand. As another example, if the artifact 110 is a button to be pressed using forefingers of the user, the artifact 110 may be reachable in one orientation but not in the other.

Figure 2A:
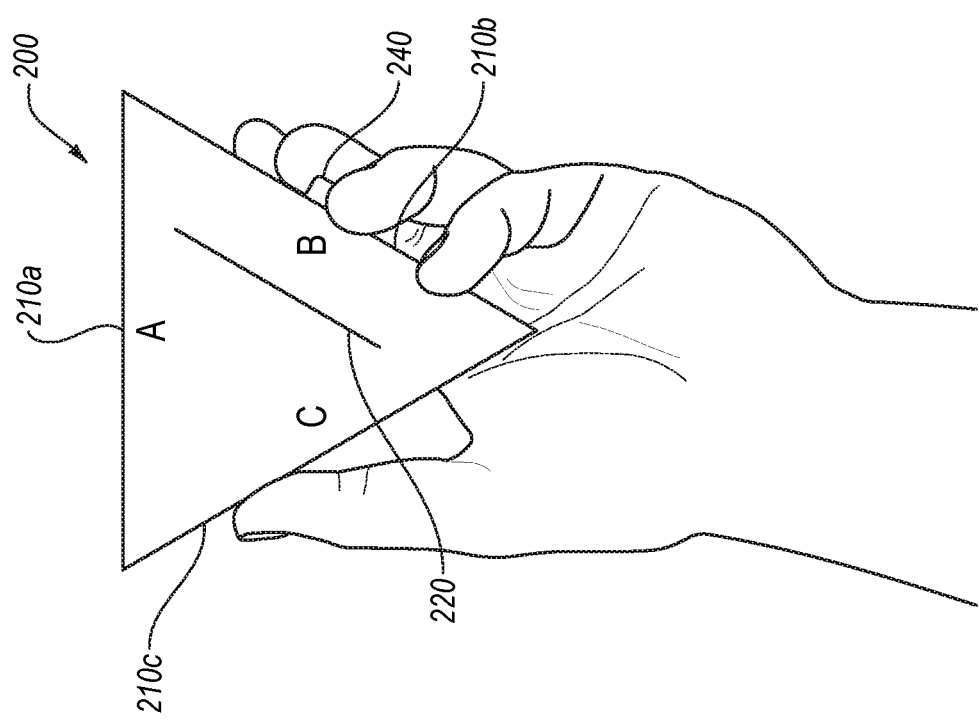

FIGS. 2A and 2B illustrate an example of another device 200 being held in left and right hands, respectively, in accordance with one or more embodiments of the present disclosure. As illustrated in FIGS. 2A and 2B, the device 200 includes three sides, side A 210a, side B 210b, and side C 210c. Additionally, the device 200 may include a display screen 220. FIG. 2A illustrates the device 200 when held in a left hand, and FIG. 2B illustrates the device 200 when held in a right hand.

As illustrated in FIG. 2A, when held in the left hand, the side A 210a may be oriented upwards, with the screen 220 parallel with side B 210b against the fingers of the left hand. Such an orientation of the device may cause the screen 220 to be tilted up and towards a face of the user.

As illustrated in FIG. 2B, when held in the right hand, the orientation of the side A 210a and side C 210c may be changed with respect to their orientation relative to the hand of the user. In particular, the side A 210a may be proximate the thumb and the side C 210c may be oriented upwards. For example, the device 200 may be rotated clockwise by approximately 120° when transitioning from the left-handed use in FIG. 2A to the right-handed use in FIG. 2B. When rotated in such a manner, the screen 220 may be oriented towards the face of the user no matter which hand the user uses. For example, the screen 220 is tilted in the direction of the thumb and upwards, regardless of whether FIG. 2A or 2B is observed. Such an orientation is possible because either side A 210a or side C 210c may be oriented upwards. This is in contrast to the device 100 of FIG. 1, in which the top face is to be oriented upwardly, regardless of which hand is used.

In some embodiments, the device 200 may include a sensor to determine which of the faces is oriented upwards. For example, the device 200 may include an accelerometer, a gyroscope, or any other sensor that facilitates determination of the orientation of the device 200. In these and other embodiments, the device 200 may include a computing device such as a processor, an ASIC, etc. to utilize the information from the sensor to control orientation of images to be displayed on the screen 220.

In some embodiments, the device 200 may include a button 240 or other feature to be interacted with using the fingers of the user. By placing the button 240 proximate the side B 210b, the button 240 remains proximate the fingers of the user regardless of whether the right or left hand is used to grasp the device.

Modifications, additions, or omissions may be made to the device 200 of FIGS. 2A and 2B without departing from the scope of the present disclosure. For example, the device 200 may include more or fewer elements than those illustrated in FIGS. 2A and 2B. As another example, while three sides are illustrated, any number of sides may be included such as six, nine, etc.

Figure 3A:
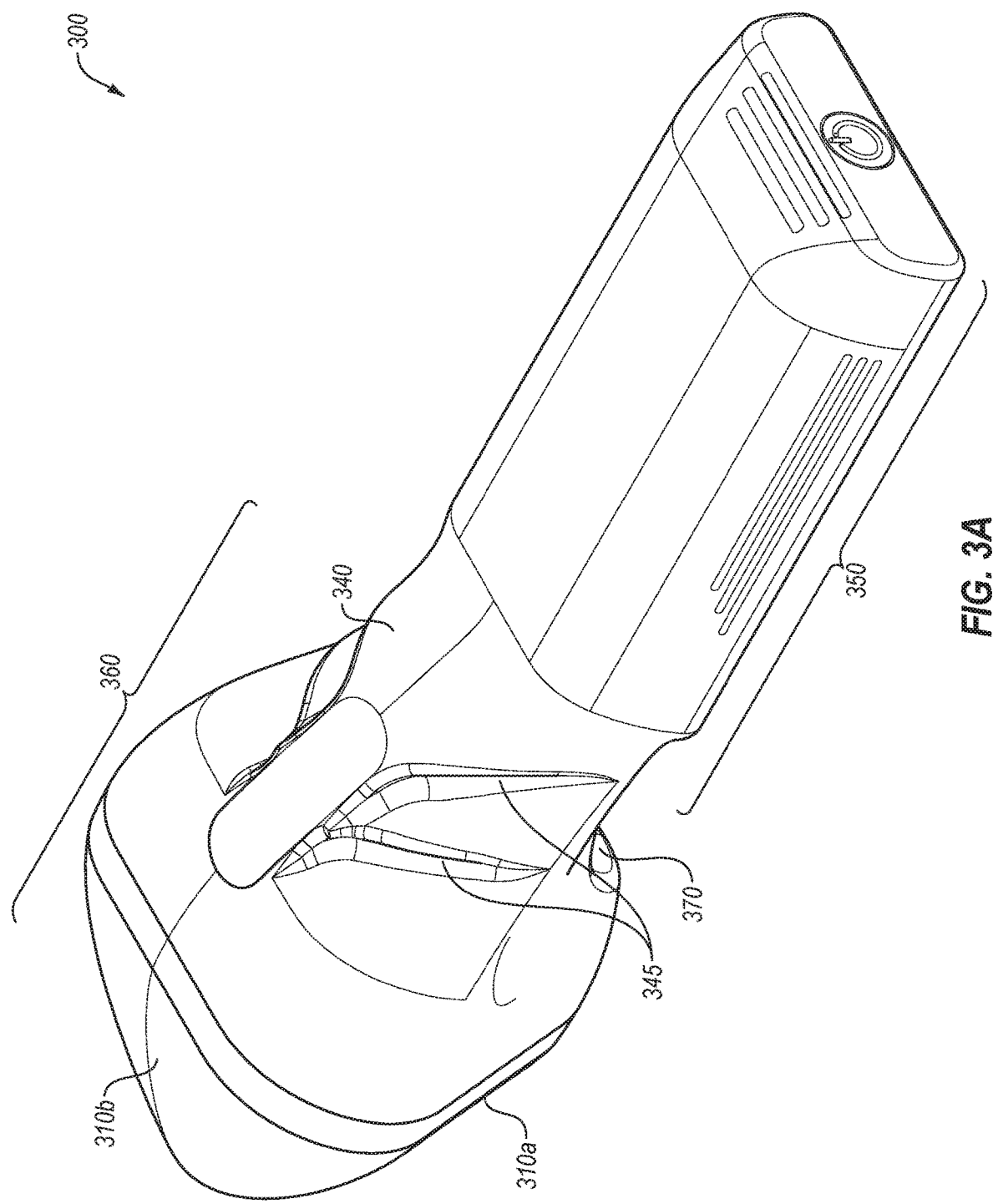
FIGS. 3A and 3B illustrate views of an example visualization device.
Figure 3B:
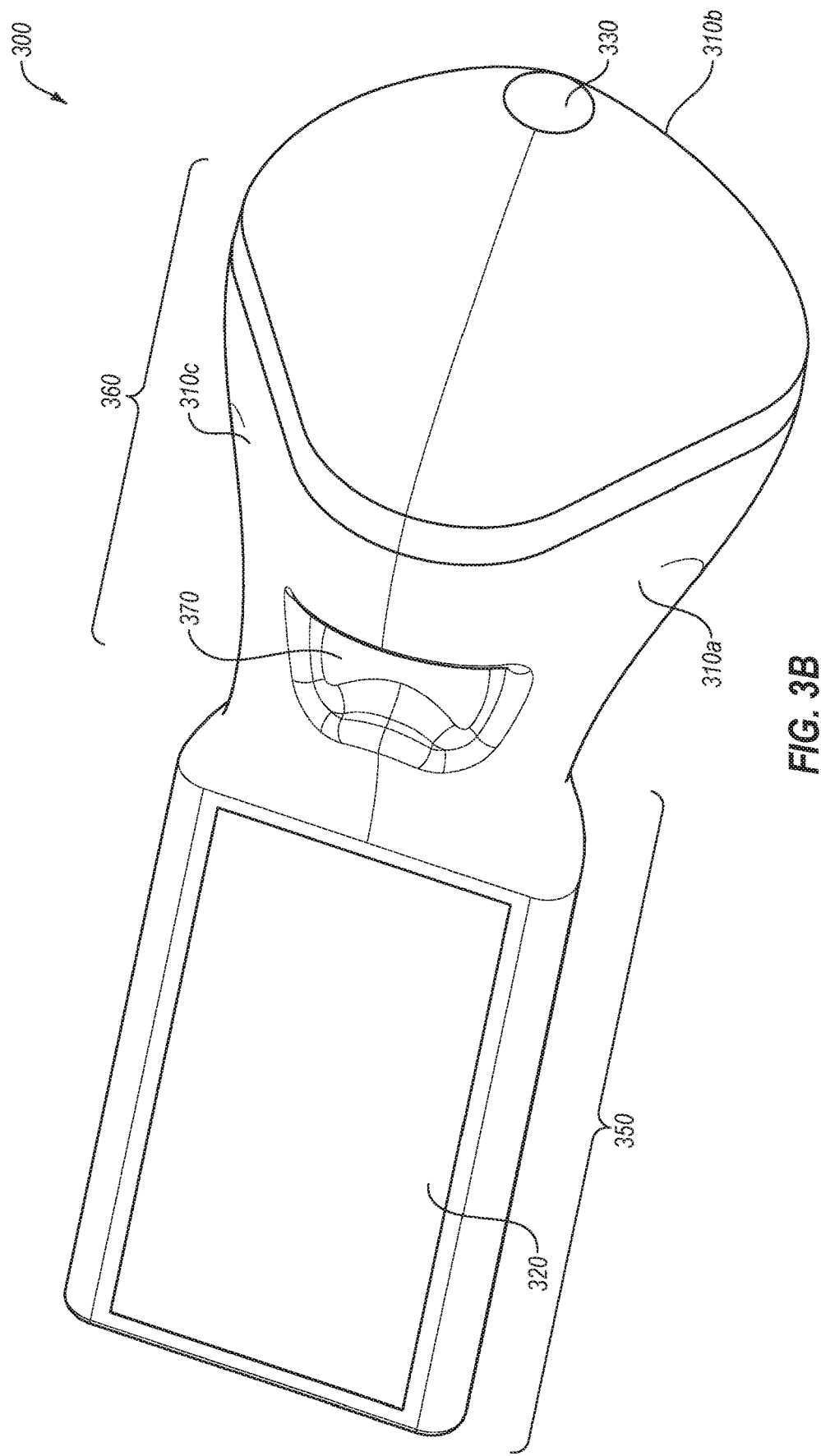

FIGS. 3A and 3B illustrate views of an example visualization device 300, in accordance with one or more embodiments of the present disclosure. The visualization device 300 may include a first side 310a, a second side 310b, and a third side 310c. The visualization device 300 may additionally include a screen 320. The screen 320 may be parallel with the second side 310b, with the first and third sides 310a and 310c extending away from the second side 310b (e.g., projecting away from an inside face of the visualization device 300). In some embodiments, the three sides may form an isosceles triangle, with the first and third sides 310a and 310c forming the equal sides of the isosceles triangle when viewed along a longitudinal axis of the device 300. Stated another way, the combination of the first side 310a, the second side 310b, and the third side 310c may form a rounded triangular pyramid.

In some embodiments, the visualization device 300 may include a sensing device 330 at or near an apex of the rounded triangular pyramid. The sensing device 330 may be any device utilized in the sensing, imaging, visualization, etc. of a subject, such as the eye of an individual. For example, the sensing device 330 may sense a property of the eye by capturing one or more images of the eye. In some embodiments, the sensing device may include one or more digital cameras (e.g., a charge-coupled device (CCD), a complementary metal-oxide semiconductor (CMOS) sensor, etc.), an infrared (IR) scanner, etc. In some embodiments, the sensing device 330 may include multiple imaging devices and/or illuminating devices disposed within the head region 360 of the visualization device 300. In these and other embodiments, the multiple imaging devices and/or illuminating devices may operate to image the eye through the apex of the rounded triangular pyramid. For example, the imaging devices and/or illuminating devices may be offset from a central axis of the eye such that the imaging devices and/or illuminating devices operate in combination to image the eye through the apex. In some embodiments, the sensing device 330 may include a covering or casing that may interface physically with, or be in close proximity to, the eye of the individual. In some embodiments, such a covering or casing may be disposable.

As illustrated in FIGS. 3A and 3B, the shape of the visualization device 300 may be described from the sensing device 330 (a proximal end of the visualization device 300) to the far side of the screen 320 (a distal end of the visualization device 300). At the distal end of the visualization device 300, the visualization device 300 may include a generally flat/rounded rectangular shape with a screen on an interior face (e.g., the face oriented towards the first side 310a and the third side 310c. The portion of the visualization device 300 with the screen 320 may be referred to as a panel region 350 of the visualization device 300. Progressing towards the proximal end of the visualization device 300, the visualization device 300 may include a generally rounded triangular pyramidal shape tapering towards the sensing device 330. The triangular pyramidal shape may begin at some point along the length of the visualization device 300, such as around half the length of the device, two thirds of the length of the device, three quarters of the length of the device, etc. such that the head region 360 may span between one fourth and one half of an overall length of the visualization device 300. The portion of the visualization device 300 with the triangular pyramidal shape may be referred to as a head region 360 of the visualization device 300. In some embodiments, the second side 310b may be generally contiguous with the panel region 350, which may include a transition from the panel region 350 to the second side 310b. For example, the panel region 350 may be generally perpendicular to a base plane of the triangular pyramidal shape of the head region 360, and the second side 310b may share the edge of the base plane with the panel region 350.

In some embodiments, the visualization device 300 may include a rounded fin 340 along the second side 310b along some portion of the length of the visualization device 300. For example, the fin 340 may begin near the base of the rounded triangular pyramid and extend in a distal direction away from the rounded triangular pyramid for a majority of the length of the remainder of the visualization device 300, although the fin 340 may extend beyond any portion of the length of the visualization device 300. In some embodiments, the fin 340 may function as a transition region between the head region 360 and the panel region 350. In some embodiments, the fin 340 may include finger grooves 345 or other tactile features to facilitate gripping of the visualization device 300 with either hand. For example, the finger grooves 345 may be generally symmetrical on both sides of the visualization device 300 such that the finger grooves 345 are available to either the left or the right hand of a user of the visualization device 300.

In some embodiments, the screen 320 may be adjustable to facilitate a better view by an operator. For example, the screen 320 may be tiltable in or out of the plane of the panel region 350. In some embodiments, such tilting may be vertically or horizontally. Such tilting may facilitate viewing the screen 320 by taller or shorter users. In some embodiments, such tilting may be between zero and thirty degrees.

In some embodiments, the visualization device 300 may include a thumb pad 370 or other thumb-receiving portion. For example, the thumb pad 370 may be recessed inwards to receive the thumb of a user of the visualization device 300. The thumb pad 370 may be generally symmetrical on both sides of the visualization device 300 such that a user of the visualization device may use either a right or left hand when operating the device. Additionally or alternatively, the thumb pad 370 may take any other physical form factor. For example, the thumb pad 370 may include two recessed or projecting regions, one that is used for receiving the thumb of a right-handed user and one that is used for receiving the thumb of a left-handed user. As another example, the thumb pad may project outwards from the face that includes the screen and towards the other faces, with a divider between two regions of the thumb-receiving portion such that one side of the divider receives and/or interfaces with the thumb when used in a right-handed orientation and the other side of the divider receives and/or interfaces with the thumb when used in a left-handed orientation. In some embodiments, the thumb pad may include a projecting spine through the thumb pad in approximately the middle of the thumb pad to separate the thumb-receiving portions for the right and left thumbs. In some embodiments, the projecting spine may span from the head region to the panel region of a visualization device.

Modifications, additions, or omissions may be made to the visualization device 300 of FIGS. 3A and 3B without departing from the scope of the present disclosure. For example, the visualization device 300 may include more or fewer elements than those illustrated in FIGS. 3A and 3B.

Figure 4:
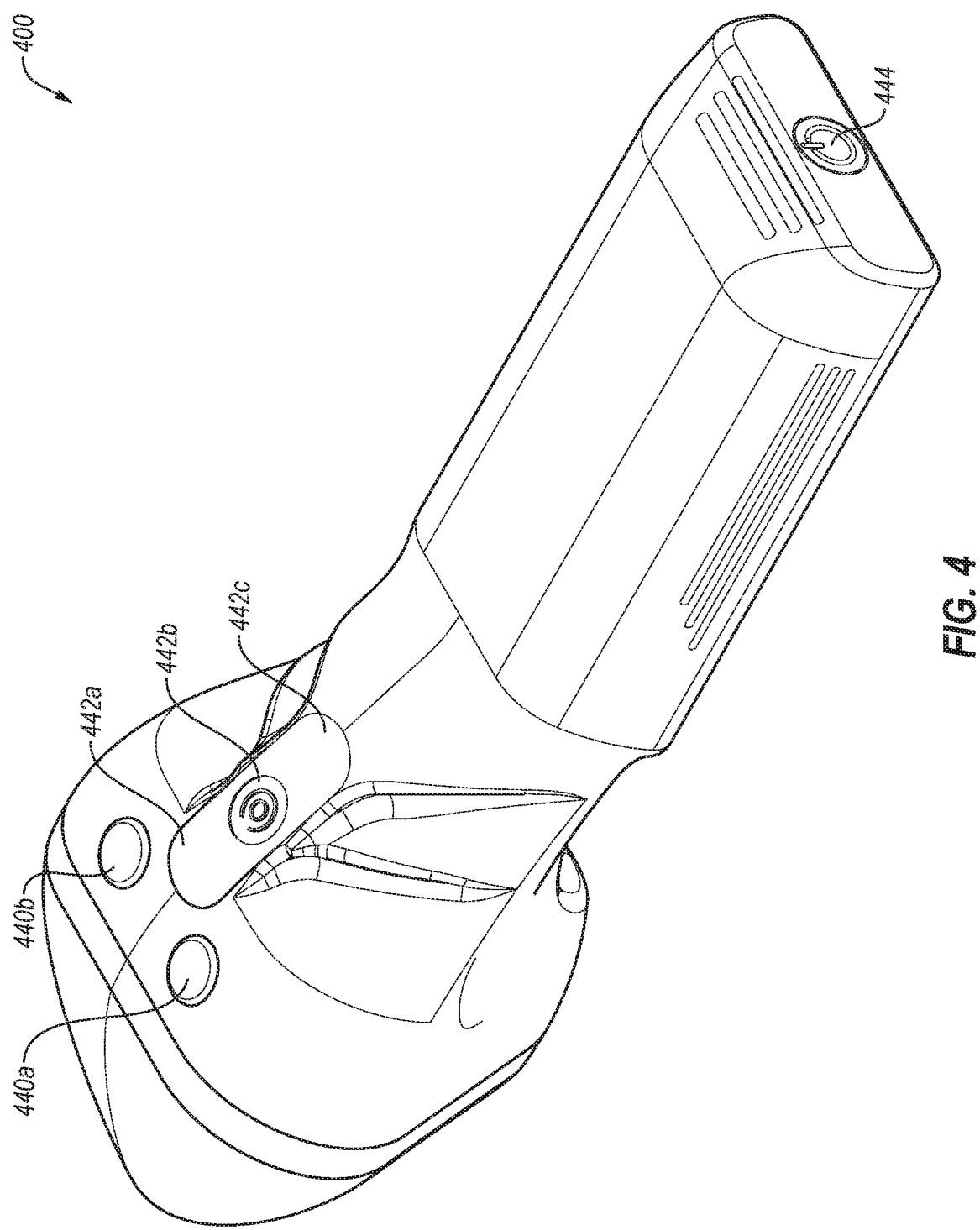
FIG. 4 illustrates various buttons on the visualization device of FIGS. 3A and 3B.

FIG. 4 illustrates various buttons on a visualization device 400 that is similar or comparable to the visualization device 300 of FIGS. 3A and 3B, in accordance with one or more embodiments of the present disclosure. The visualization device 400 may include a number of buttons, such as the buttons 440a, 440b, and/or 442 along the back side of the visualization device 400 such that a user may press the buttons with their forefinger, regardless of which hand the user is using. For example, as illustrated in both FIGS. 2A and 2B, the side B 210b may be oriented proximate the fingers of the user. Thus, the buttons may be located and/or oriented in a manner that they may be pressed regardless of which hand is used.

The locations of the buttons 440a, 440b, and/or 442 are merely examples of locations of buttons, such as locations where buttons may be invoked by the user regardless of which hand they are using. Buttons such as 440a, 440b and/or 442 may be mechanical buttons, fixed force sensors with haptic feedback, or any equivalent form of button. As another example, button 442 could be a force sensor strip with haptic feedback such that the center of button strip 442b has a different function when depressed compared to the ends of the button strip 442a/442c. Another example location of a button may include the button 444. In some embodiments, the button 444 may operate to turn the visualization device 400 on or off. In some embodiments, the button 444 may be configured to vertically invert any image displayed on the screen. For example, the button 444 may provide a manual feature by which the user may switch the handedness of the visualization device 400 by changing the orientation of an image on the screen. Additionally or alternatively, manual switching of the image on the screen may take place using software buttons in the user interface on the screen if the screen is a touchscreen.

Modifications, additions, or omissions may be made to the visualization device 400 of FIG. 4 without departing from the scope of the present disclosure. For example, the visualization device 400 may include more or fewer elements than those illustrated in FIG. 4. For example, the visualization device 400 may include any number of buttons in any configuration.

Figure 5B:
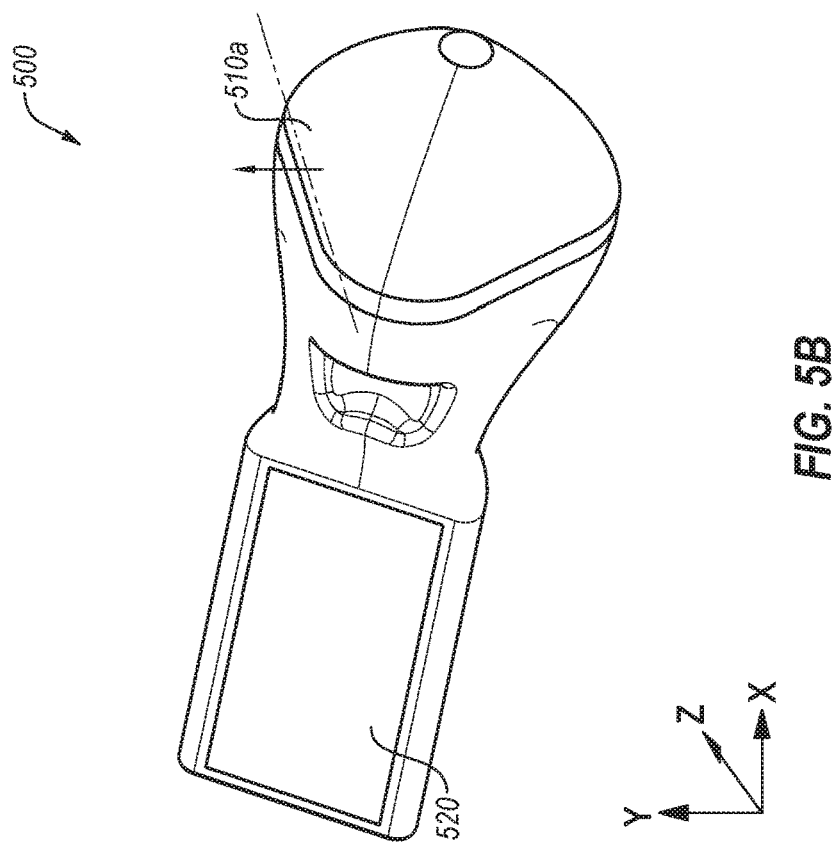
FIGS. 5A and 5B illustrate orientations of the example visualization device of FIGS. 3A and 3B.
Figure 5A:
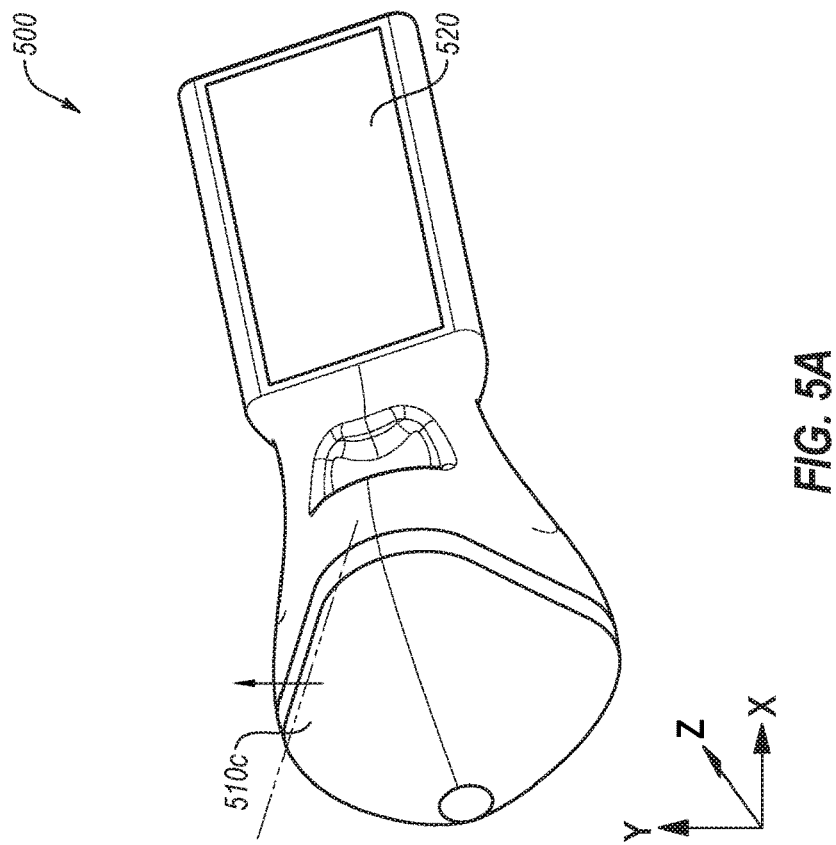

FIGS. 5A and 5B illustrate orientations of an example visualization device 500 that may be similar or comparable to the visualization device 300 of FIGS. 3A and 3B and/or the visualization device 400 of FIG. 4, in accordance with one or more embodiments of the present disclosure.

As illustrated in FIG. 5A, when oriented with the side 510c oriented upwards (as noted by the arrow pointing upwards from the side 510c being parallel with the y-axis of the coordinate system), the screen 520 may be tilted upwards in a first direction. The dashed line indicates a line along the side 510c that may be generally parallel with the ground (e.g., generally parallel with the x-z plane).

As illustrated in FIG. 5B, when oriented with the side 510a pointing upwards (as noted by the arrow pointing upwards from the side 510a being parallel with the y-axis of the coordinate system), the screen 520 may be tilted upwards in a second direction that is rotated approximately 120° relative to the first direction. The dashed line indicates a line along the side 510a that may be generally parallel with the ground (e.g., generally parallel with the x-z plane).

Modifications, additions, or omissions may be made to the visualization device 500 of FIGS. 5A and 5B without departing from the scope of the present disclosure. For example, the visualization device 500 may include more or fewer elements than those illustrated in FIGS. 5A-5B.

Figure 6B:
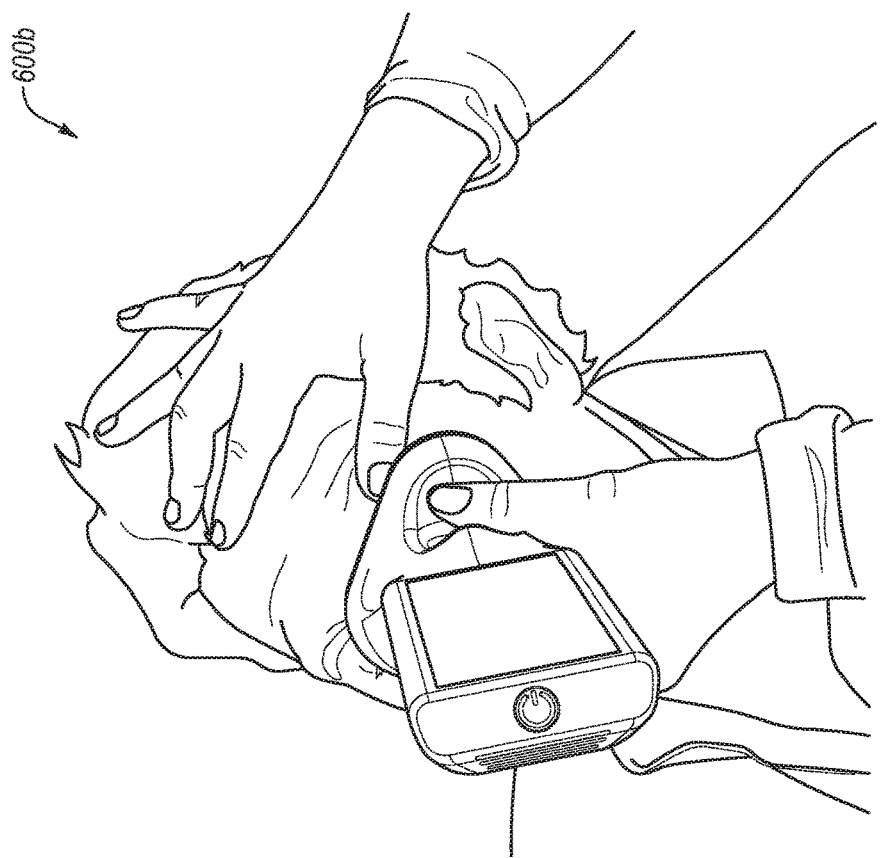
FIGS. 6A and 6B illustrate various examples of use of a visualization device.
Figure 6A:
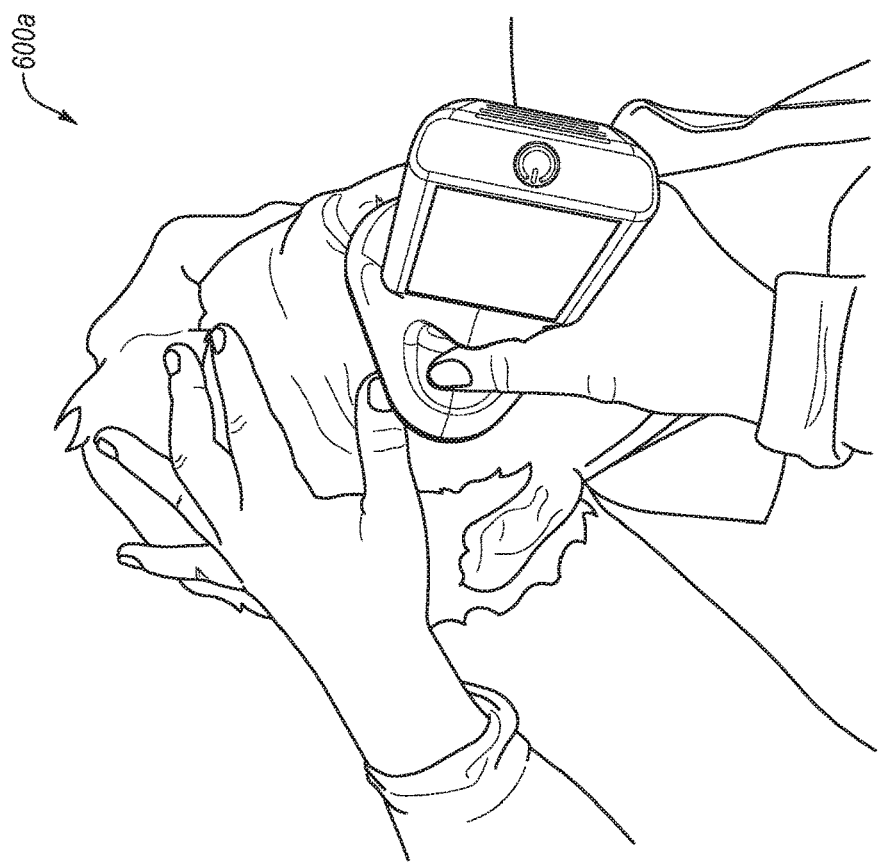

FIGS. 6A and 6B illustrate various examples 600a and 600b, respectively, of use of a visualization device, in accordance with one or more embodiments of the present disclosure.

As illustrated in FIG. 6A, the visualization device may be used in the right hand of a user to image an eye of an individual. When used in this orientation, the screen may face the user. As illustrated in FIG. 6C, the visualization device may be used in the left hand of a user to image an eye of an individual. When used in this orientation, again the screen may face the user, despite the visualization device being used in the other hand.

Figure 7A:
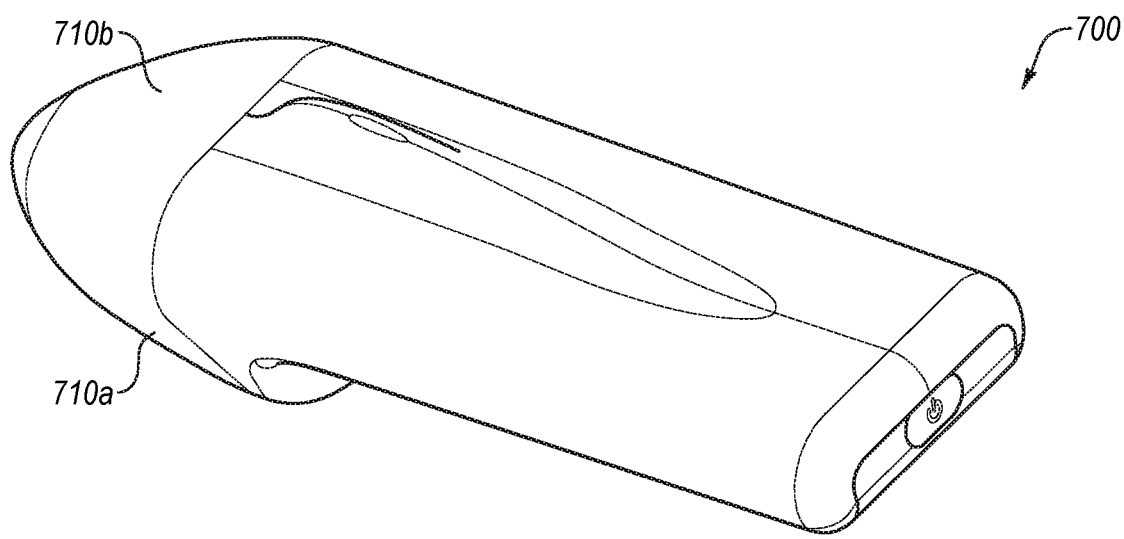
FIGS. 7A and 7B illustrate another example visualization device.
Figure 7B:
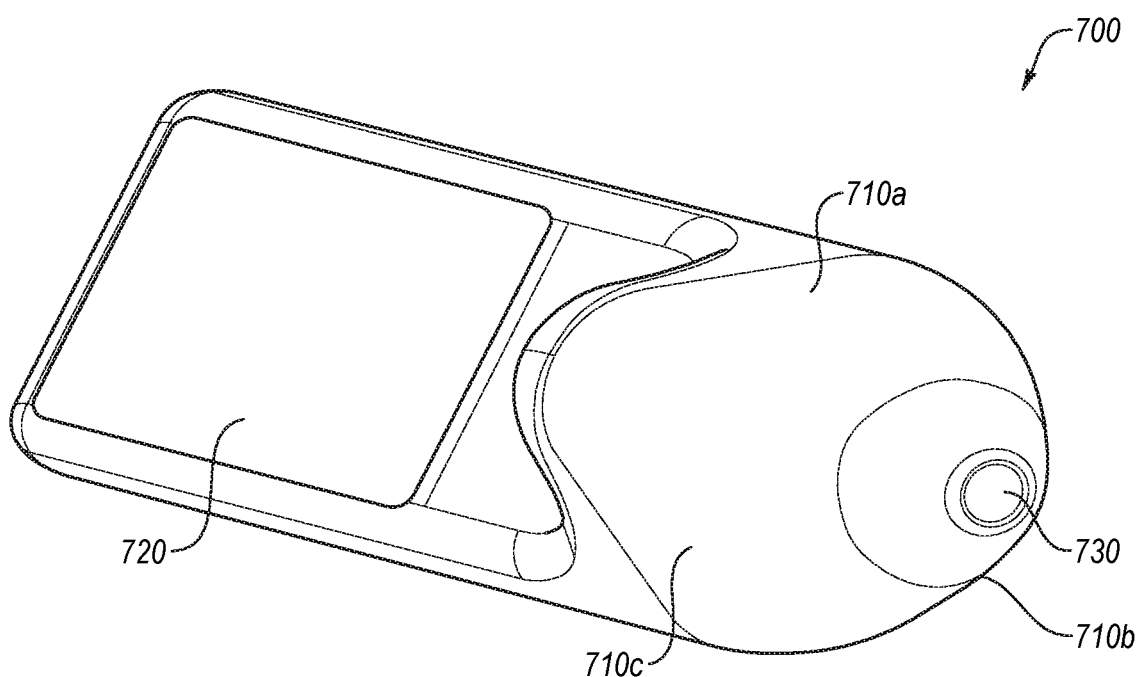

FIGS. 7A and 7B illustrate views of another example visualization device 700, in accordance with one or more embodiments of the present disclosure. In operation, the visualization device 700 may be similar and/or comparable to the visualization devices 300 of FIGS. 3A and 3B and/or the visualization device 400 of FIG. 4. For example, the visualization device 700 may include a first side 710a, a second side 710b, and a third side 710c. The visualization device 700 may additionally include a screen 720. The screen 720 may be on a plane that shares an edge with the second side 710b, with the first and third sides 710a and 710c extending away from the second side 710b. The first, second, and third sides 710a-710c may operate and be oriented in a similar manner to the sides of the visualization device 300 of FIG. 3.

In some embodiments, the screen may be a removable device with physical connectors that couple with the rest of the visualization device. In these and other embodiments, the screen may be removed (e.g., slid out of a slot) and replaced in a different orientation to facilitate the use of the visualization device in either hand. For example, the screen may be pulled out of a slot to remove the screen from the device, rotated 180°, and reinserted in the slot. In such an embodiment, the screen may include physical connectors on two ends of the screen and may utilize a cover to be placed over the physical connectors not in use. In these and other embodiments, the physical connectors may operate as data exchange ports such that images and/or other information sensed or gathered by the visualization device may be conveyed to the screen. For example, display data from the visualization device may be conveyed to the display via the data exchange ports such that the display visually depicts information from the visualization device. Additionally or alternatively, information from the screen may be communicated to the visualization device via the data exchange ports. Additionally or alternatively, the screen may include a wireless communication device (e.g., near field communications, Bluetooth, etc.) such that when removed and the orientation changed, no physical connectors are used or changed to communicatively couple the screen with the visualization device. Additionally or alternatively, the screen may be removed from its primary position, rotated 180 degrees, and returned to its primary position using a flexible joint or hinge rather than physically separating the screen from the device entirely. For example, the panel region may be spring-biased or otherwise biased against the head region of the device. The panel region may be pulled away from the head region in a manner where the panel region is still connected but overcomes the spring-biasing or other biasing force such that the panel region may be rotated and then released to again be biased against the head region. For example, the head region may include a groove or slot in which the panel region rests prior to being pulled outward and rotated.

In some embodiments, devices of the present disclosure may include a computing device (not illustrated). Such a computing device may be configured to facilitate the performance of the operations described herein, such as capturing images or scans of an eye, rotating, inverting, or otherwise changing the orientation of an image on a screen, receiving data from a sensor such as a gyroscope or accelerometer, using such data to determine an orientation of a device, displaying images that are acquired, displaying warnings or user interface elements that facilitate use of the device, etc. Such a computing device may include a processor, a memory, etc. and may be in communication with and/or part of a visualization device.

Generally, the processor may include any suitable special-purpose or general-purpose computer, computing entity, or processing device including various computer hardware or software modules and may be configured to execute instructions stored on any applicable computer-readable storage media. For example, the processor may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

It is understood that the processor may include any number of processors distributed across any number of networks or physical locations that are configured to perform individually or collectively any number of operations described herein. In some embodiments, the processor may interpret and/or execute program instructions and/or processing data stored in the memory. By interpreting and/or executing program instructions and/or process data stored in the memory, the device may perform operations, such as the operations performed by the devices described in the present disclosure.

The memory may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. In these and other embodiments, the term "non-transitory" as used herein should be construed to exclude only those types of transitory media that were found to fall outside the scope of patentable subject matter in the Federal Circuit decision of In re Nuijten, 500 F.3d 1346 (Fed. Cir. 2007). In some embodiments, computer-executable instructions may include, for example, instructions and data configured to cause the processor to perform a certain operation or group of operations as described in the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A device, comprising:
   a display screen;
   a generally triangular shaped body with first, second, and third sides, the display screen generally parallel with the first side, and the device configured such that either of the second side and the third side may be oriented generally upwards during operation;
   a sensing device at an apex of the generally triangular shaped body, the sensing device configured to sense a property of an eye;
   a sensor configured to detect whether the second or the third side is oriented generally upwards; and
   a computing device configured to orient an image to be displayed on the display screen based on whether the second or the third side is oriented generally upwards.

2. The device of claim 1, further comprising a panel region proximate the display screen and projecting away from the generally triangular shaped body.

3. The device of claim 2, wherein the panel region is generally contiguous with the first side of the generally triangular shaped body.

4. The device of claim 2, further comprising thumb pad spanning between the generally triangular shaped body and the panel region, the thumb pad shaped to interface with a thumb of either a left hand or a right hand.

5. The device of claim 4, wherein the thumb pad is recessed into a casing of the device.

6. The device of claim 1, further comprising a disposable casing covering the sensing device.

7. The device of claim 6, wherein the sensing device includes a plurality of imaging devices that image an eye through the apex of the generally triangular shaped body.

8. The device of claim 1, wherein the display screen is removable.

9. The device of claim 1, wherein the display screen is configured to tilt between zero and thirty degrees, the tilt moving an edge of the display screen away from or in towards a plane of the first side.

10. The device of claim 1, wherein the generally triangular shaped body includes a rounded triangular pyramid shaped body.

11. The device of claim 1, wherein the generally triangular shaped body spans between one fourth and one half of an overall length of the device.

12. The device of claim 1, further comprising a fin or finger grip region along a back side of the device, the back side of the device opposite from the display screen.

13. The device of claim 12, further comprising one or more buttons on the back side of the device proximate the fin or finger grip region for controlling operation of the device.

14. The device of claim 1, wherein the computing device is configured to orient the image such that a top of the image is oriented towards the second side when the second side is generally oriented upwards and the top of the image is oriented towards the third side when the third side is generally oriented upwards.

15. A device, comprising:
   a rounded triangular pyramid shaped body with first, second, and third sides, the device configured such that either of the second side and the third side may be oriented generally upwards during operation;
   a panel region projecting away from the rounded triangular pyramid and perpendicular with a plane of a base of the rounded triangular pyramid, the panel region including a slot with an opening at a distal end and a first data exchange port at a proximate end, the proximate end proximate the rounded triangular pyramid; and
   a removable display screen shaped to slide through the opening and into the slot of the panel region, the removable display screen including a second data exchange port on a first end and a third data exchange port on a second end opposite the first end, the second and third data exchange ports configured to interface with the first data exchange port such that display data of the device is displayed on the removable display screen.

16. The device of claim 15, wherein the removable display screen is generally symmetrical about a line from the first end to the second end aside from a location of the second and third data exchange ports.

17. The device of claim 15, further comprising a sensing device, the sensing device including a plurality of imaging device configured to image an eye through an apex of the rounded triangular pyramid.

18. The device of claim 15, wherein the removable display screen is configured to display an image of the display data in a first orientation if the first data exchange port is interfaced with the second data exchange port and in a second orientation if the first data exchange port is interface with the third data exchange port, the second orientation inverted relative to the first orientation.

19. A device, comprising:
   a multi-sided body with at least first, second, and third sides, the device configured such that either of the second side and the third side may be oriented generally upwards during operation;
   a panel region extending away from the multi-sided body and perpendicular with a plane of a base of the multi-sided body;

a display screen disposed on an inside face of the panel region and parallel with the first side;
a sensor configured to detect whether the second or the third side is oriented generally upwards; and
a computing device configured to orient an image to be displayed on the display screen based on whether the second or the third side is oriented generally upwards.

\* \* \* \* \*